(12) United States Patent
Park et al.

(10) Patent No.: US 10,349,919 B2
(45) Date of Patent: Jul. 16, 2019

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Jin-ki Park, Hongcheon-gun (KR); Jin-yong Lee, Hongcheon-gun (KR); Hyuk-jae Chang, Seoul (KR); Namsik Chung, Seoul (KR); Geu-ru Hong, Seoul (KR); Chi-young Shim, Seoul (KR); Ji-hyun Yoon, Seoul (KR); In-jeong Cho, Seoul (KR); Ran Heo, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 442 days.

(21) Appl. No.: 15/091,338

(22) Filed: Apr. 5, 2016

(65) Prior Publication Data
US 2017/0049419 A1  Feb. 23, 2017

(30) Foreign Application Priority Data

Aug. 18, 2015  (KR) ........................ 10-2015-0116100

(51) Int. Cl.
*A61B 8/08* (2006.01)
*A61B 8/00* (2006.01)
(Continued)

(52) U.S. Cl.
CPC ............ *A61B 8/5223* (2013.01); *A61B 5/055* (2013.01); *A61B 6/032* (2013.01); *A61B 6/504* (2013.01);
(Continued)

(58) Field of Classification Search
CPC ....... A61B 8/464; A61B 8/5223; A61B 8/483; A61B 8/5207; A61B 8/488; A61B 8/463;
(Continued)

(56) References Cited

U.S. PATENT DOCUMENTS 7,627,156 B2   12/2009   Margolis et al.
8,077,939 B2   12/2011   Le Nezet et al.
(Continued)

FOREIGN PATENT DOCUMENTS

JP   2011-036458 A   2/2011
JP   2011-72500 A    4/2011
(Continued)

OTHER PUBLICATIONS

Brajesh K. Lal et al., "Pixel distribution analysis of B-mode ultrasound scan images predicts histologic features of atherosclerotic carotid plaques", Journal of Vascular Surgery, vol. 35, Issue 6, p. 1210-1217, Jun. 2002.*
(Continued)

*Primary Examiner* — Peter Luong
(74) *Attorney, Agent, or Firm* — Sughrue Mion, PLLC

(57) ABSTRACT

Provided is an ultrasound diagnosis apparatus including a data acquirer configured to obtain ultrasound data about an object having blood vessels; an image processor configured to extract a blood vessel area from an ultrasound image generated based on the ultrasound data, extract a plaque area included in the blood vessel area, and analyze a risk of plaque based on at least one of a surface shape of the plaque area and brightness information of the plaque area; and a display configured to display the risk of plaque.

18 Claims, 12 Drawing Sheets

(51) Int. Cl.
    *A61B 5/055* (2006.01)
    *A61B 6/03* (2006.01)
    *A61B 6/00* (2006.01)

(52) U.S. Cl.
    CPC .......... *A61B 8/0891* (2013.01); *A61B 8/4405* (2013.01); *A61B 8/4427* (2013.01); *A61B 8/4461* (2013.01); *A61B 8/4472* (2013.01); *A61B 8/4477* (2013.01); *A61B 8/463* (2013.01); *A61B 8/464* (2013.01); *A61B 8/467* (2013.01); *A61B 8/483* (2013.01); *A61B 8/488* (2013.01); *A61B 8/5207* (2013.01); *A61B 8/565* (2013.01); *A61B 8/085* (2013.01); *A61B 2560/0475* (2013.01)

(58) Field of Classification Search
    CPC ....... A61B 8/0891; A61B 8/467; A61B 8/565; A61B 8/4405; A61B 8/4427; A61B 8/4461; A61B 8/4477; A61B 8/4472; A61B 8/085; A61B 6/504; A61B 6/032; A61B 5/055; A61B 2560/0475
    See application file for complete search history.

(56) References Cited

U.S. PATENT DOCUMENTS

| | | | |
|---|---|---|---|
| 8,718,344 | B2 | 5/2014 | Kobayashi et al. |
| 8,744,151 | B2 | 6/2014 | Hirano et al. |
| 2002/0115931 | A1* | 8/2002 | Strauss .................... A61B 5/06 600/420 |
| 2008/0119713 | A1 | 5/2008 | Le Nezet et al. |
| 2011/0125034 | A1* | 5/2011 | Tsuji .................. A61B 5/02007 600/485 |
| 2012/0189181 | A1 | 7/2012 | Hirano et al. |
| 2013/0046168 | A1* | 2/2013 | Sui ...................... A61B 5/0035 600/411 |
| 2015/0196271 | A1 | 7/2015 | Nair |

FOREIGN PATENT DOCUMENTS

| | | |
|---|---|---|
| JP | 2012-016575 A | 1/2012 |
| JP | 2013-052131 A | 3/2013 |
| JP | 5436125 B2 | 3/2014 |
| JP | 2014-094157 A | 5/2014 |
| JP | 2015-6260 A | 1/2015 |

OTHER PUBLICATIONS

Pranvera Ibrahimi et al., "Vulnerable plaques in the contralateral carotid arteries in symptomatic patients: A detailed ultrasound analysis", Elsevier, Atherosclerosis 235, 2014, (pp. 526-531) XP028879014.

Baris Kanber et al., "Quantitative assessment of carotid plaque surface irregularities and correlation to cerebrovascular symptoms", Cardiovascular Ultrasound 2013; 11:38, vol. 11, (8 Pages Total) URL: http://www.cardiovascularultrasound.com/content/11/1/38 doi:10.1186/1476-7120-11-38.

Shyam Prabhakaran, MD. et al., "Carotid Plaque Surface Irregularity Predicts Ischemic Stroke: The Northern Manhattan Study", Stroke, Journal of the American Heart Association, vol. 37, Nov. 2006 (pp. 2696-2701, 7 Total Pages) XP055334298, DOI: 10.1161/01.STR.0000244780.82190.a4.

Michael M. Sabetai, MD. et al., "Hemispheric symptoms and carotid plaque echomorphology", Journal of Vascular Surgery, vol. 31, No. 1, Part 1, (pp. 39-49), 2000 XP027398328.

S.K. Kakkos et al., "Texture Analysis of Ultrasonic Images of Symptomatic Carotid Plaques can Identify Those Plaques Associated with Ipsilateral Embolic Brain Infarction", European Journal of Vascular and Endovascular Surgery(Eur J Vasc Endovasc Surg) vol. 33, (pp. 422-429), 2007 XP022014244, doi:10.1016/j.ejvs.2006.10.018.

N. El-Barghouty et al., "The Identification of the High Risk Carotid Plaque", European Journal of Vascular and Endovascular Surgery(Eur J Vasc Endovasc Surg) vol. 11, W. B . Saunders Company LTD., (pp. 470-478), 1996, XP005067557.

Communication dated Jan. 24, 2017, from the European Patent Office in counterpart European Application No. 16162799.7.

* cited by examiner

ULTRASOUND DIAGNOSIS APPARATUS AND METHOD OF OPERATING THE SAME

CROSS-REFERENCE TO RELATED APPLICATION

This application claims the benefit of Korean Patent Application No. 10-2015-0116100, filed on Aug. 18, 2015, in the Korean Intellectual Property Office, the disclosure of which is incorporated herein in its entirety by reference.

BACKGROUND

1. Field

One or more exemplary embodiments relate to an ultrasound diagnosis apparatus and a method of operating the ultrasound diagnosis apparatus, and more particularly, to an ultrasound diagnosis apparatus capable of displaying a risk of plaque in a blood-vessel ultrasound image and a method of operating the ultrasound diagnosis apparatus.

2. Description of the Related Art

Ultrasound diagnosis apparatuses transmit ultrasound signals generated by transducers of a probe to an object and receive echo signals reflected from the object, thereby capturing at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses operate with high stability, display images in real time, and are safe due to the lack of radioactive exposure, unlike X-ray apparatuses. Therefore, ultrasound imaging apparatuses are widely used together with other image diagnosis apparatuses.

In addition, an ultrasound diagnosis apparatus may provide a brightness (B) mode showing a reflective coefficient of an ultrasound signal reflected by an object in a two-dimensional (2D) image, a Doppler mode showing an image of a moving object (in particular, blood flow) by using a Doppler effect, and an elastic mode showing an image representing a difference between reactions when compression is applied and not applied to an object.

SUMMARY

One or more exemplary embodiments include an ultrasound diagnosis apparatus capable of extracting a plaque area from a blood-vessel ultrasound image and representing a risk of plaque in various ways, and a method of operating the ultrasound diagnosis apparatus.

Additional aspects will be set forth in part in the description which follows and, in part, will be apparent from the description, or may be learned by practice of the presented embodiments.

According to one or more exemplary embodiments, an ultrasound diagnosis apparatus includes: a data acquirer configured to obtain ultrasound data about an object having blood vessels; an image processor configured to extract a blood vessel area from an ultrasound image generated based on the ultrasound data, extract a plaque area included in the blood vessel area, and analyze a risk of plaque based on at least one of a surface shape of the plaque area and brightness information of the plaque area; and a display configured to display the risk of plaque.

The image processor may calculate a smoothness index (SI) representing a surface uniformity of the plaque area, and analyze the risk of plaque based on the surface uniformity of the plaque area, and the risk of plaque is determined to be low when a surface of the plaque area is uniform and is determined to be high when the surface of the plaque area is not uniform.

The image processor may measure distances from a surface of a blood vessel to a surface of the plaque area in at least one of a circumferential direction and a lengthwise direction of the blood vessel, and calculate the SI of the plaque area based on distribution of the measured distances.

The brightness information of the plaque area may include a brightness level of the plaque area and a distribution state of brightness values in the plaque area, and the risk of plaque may be determined to be high when the brightness level of the plaque area is equal to or greater than a first critical value or less than a second critical value that is less than the first critical value and a determined to be low when the brightness level of the plaque area is less than the first critical value and equal to or greater than the second critical value, and the brightness values may be evenly distributed.

The image processor may calculate the brightness level of the plaque area and the distribution state of the brightness values, based on a histogram of the brightness values in the plaque area.

A value representing the distribution state of the brightness values may be calculated based on at least one of a median value, an average value, a minimum value, a maximum value, a distribution value, and a standard deviation calculated from the histogram.

The display may represent the risk of plaque by using at least one of a color, a graph, and a numerical value.

The display may indicate on a first region included in the plaque area a first color corresponding to a risk of plaque in the first region on the first region included in the plaque area, and indicate a second color on a second region included in the plaque area corresponding to a risk of plaque in the second region.

The display may mark an icon on a region having a higher risk between the first region and the second region.

The display may indicate the distribution state of the brightness values in the plaque area as a texture.

According to one or more exemplary embodiments, a method of operating an ultrasound diagnosis apparatus, the method includes: obtaining ultrasound data about an object having blood vessels; extracting a blood vessel area from an ultrasound image generated based on the ultrasound data, and extracting a plaque area included in the blood vessel area; analyzing a risk of plaque based on at least one of a surface shape of the plaque area and brightness information of the plaque area; and displaying the risk of plaque.

The analyzing of the risk of plaque may include: calculating a smoothness index (SI) representing a surface uniformity of the plaque area; and analyzing the risk of plaque based on the surface uniformity of the plaque area, wherein the risk of plaque may be determined to be low when the surface of the plaque area is uniform, and determined to be high when the surface of the plaque area is not uniform.

The calculating of the SI may include: measuring distances from a surface of the blood vessel to the surface of the plaque area in at least one of a circumferential direction and a lengthwise direction of the blood vessel; and calculating the SI of the plaque area based on a distribution of the measured distances.

The analyzing of the risk of plaque may include calculating the brightness level of the plaque area and the distribution state of the brightness values based on a histogram of the brightness values in the plaque area.

The displaying of the risk of plaque may include indicating the risk by using at least one of a color, a graph, and a numerical value.

The displaying of the risk of plaque may include indicating on a first region included in the plaque area a first color corresponding to a risk of plaque in the first region on the first region included in the plaque area, and indicating on a second region included in the plaque area a second color corresponding to a risk of plaque in the second region.

The displaying of the risk of plaque may include marking an icon on a region having a higher risk between the first region and the second region.

The displaying of the risk of plaque may include indicating the distribution state of the brightness values in the plaque area as a texture.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
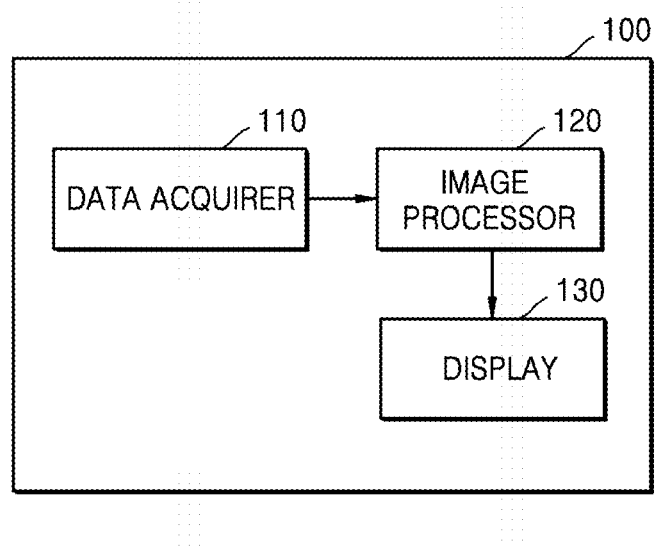
FIG. 1 is a block diagram of an ultrasound diagnosis apparatus according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein are to be defined based on the meaning of the terms together with the description throughout the specification.

Throughout the specification, it will also be understood that when a component "includes" an element, unless there is another description contrary thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, "image" may denote multi-dimensional data consisting of discrete image elements, for example, an image may include a medical image (an ultrasound image, a computed tomography (CT) image, and a magnetic resonance (MR) image) of an object, captured by an ultrasound apparatus, a CT apparatus, and a magnetic resonance imaging (MRI) apparatus, but is not limited thereto.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

An ultrasound image may denote an image obtained by irradiating an ultrasound signal generated by a transducer of a probe onto an object and receiving information of an echo signal reflected by the object. In addition, the ultrasound image may be represented in various modes. For example, an ultrasound image may be at least one of an amplitude (A) mode image, a brightness (B) mode image, a color (C) mode image, and a Doppler (D) mode image. In addition, according to an exemplary embodiment, an ultrasound image may be a two-dimensional (2D) image or a three-dimensional (3D) image.

A CT image may denote a combined image of a plurality of X-ray images obtained by photographing an object while pivoting about at least one axis with respect to an object.

An MR image may denote an image of an object obtained by using a nuclear magnetic resonance effect.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to exemplary embodiments, examples of which are illustrated in the accompanying drawings. In this regard, the present exemplary embodiments may have different forms and should not be construed as being limited to the descriptions set forth herein. As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of an ultrasound diagnosis apparatus 100 according to an exemplary embodiment. Referring to FIG. 1, the ultrasound diagnosis apparatus 100 may include a data acquirer 110, an image processor 120, and a display 130.

The data acquirer 110 according to the present exemplary embodiment may obtain ultrasound data of an object having blood vessels. For example, the data acquirer 110 transmits an ultrasound signal to the object having blood vessels, and receives an echo signal reflected by the object. The data acquirer 110 may process the echo signal to generate ultrasound data about the object having the blood vessels.

The ultrasound data may be 2D data or 3D volume data. The 2D data may represent a cross-sectional of the object, and the 3D volume data may denote data that is reconstructed as a 3D format from accumulated cross-sectional data of the object. A form of the volume data may vary depending on a kind of a probe used in the ultrasound diagnosis apparatus 100.

The data acquirer 110 may receive ultrasound data generated by an external ultrasound diagnosis apparatus, without generating the ultrasound data by itself after receiving the ultrasound signal from the object.

The image processor 120 according to the present exemplary embodiment may generate ultrasound images based on the ultrasound data. The image processor 120 may generate the ultrasound images by performing a scan conversion process on the ultrasound data obtained by the data acquirer 110.

The image processor 120 may extract and process a B mode component from the ultrasound data. The image processor 120 may generate an ultrasound image, in which an intensity of a signal is represented as brightness, based on the extracted B mode component.

In addition, the image processor 120 may extract a blood vessel area from the generated ultrasound image. Here, the image processor 120 detects edges based on pixel values included in the ultrasound image, and may detect the blood vessel area by using the detected edges. However, one or more exemplary embodiments are not limited to the above method, and the blood vessel area may be extracted from the ultrasound image by various blood vessel extraction methods that are well known in the art.

In addition, the image processor 120 may extract a plaque area included in the extracted blood vessel area. Here, the image processor 120 detects the edges based on the pixel values included in the blood vessel area, and extracts the plaque area by using the detected edges. Alternatively, a blood vessel area may be converted into a binary image by using a critical value, and a plaque area may be extracted based on the binary image. Alternatively, the ultrasound image may be converted to a polar form, and then, a plaque area may be extracted by detecting edges having high illuminance. Alternatively, a Doppler signal about a blood vessel area may be analyzed in order to detect an area where there is no Doppler signal, and a detected area may be extracted as a plaque area. Alternatively, an area having a smaller degree of deformation with respect to a pressure may be detected by using an elastic signal of the blood vessel area, and a detected area may be extracted as a plaque area.

The above methods are simply examples, and one or more exemplary embodiments are not limited to the above examples. In addition, the plaque area may be extracted from the ultrasound image by using various plaque extraction methods that are well known in the art.

The image processor 120 according to the present exemplary embodiment may analyze the risk of plaque, based on a surface shape and brightness information of the extracted plaque area.

According to the present exemplary embodiment, the risk of plaque is determined to be low when the surface of the plaque area is uniform, and the risk of plaque is determined to be high when the surface of the plaque area is not uniform. Accordingly, the image processor 120 may determine the risk of plaque according to whether the surface shape of the plaque area is uniform.

For example, the image processor 120 may calculate a smoothness index (SI) representing whether the surface shape of the plaque area is uniform. The image processor 120 measures distances from a blood vessel intima to the surface of the plaque area in a circumferential direction of the blood vessel, and may calculate the SI of the surface of the plaque area in the circumferential direction based on distribution of the measured distances.

In addition, the image processor 120 measures distances from a surface of the blood vessel intima to the surface of the plaque area in a lengthwise direction of the blood vessel, and calculates the SI of the surface of the plaque area in the lengthwise direction based on distribution of the measured distances. This will be described in more detail later with reference to FIG. 6.

In addition, according to the present exemplary embodiment, the risk of plaque may be determined to be high when the brightness of the plaque area is equal to or greater than a first critical value. For example, if the brightness of the plaque area is equal to or greater than the first critical value, the plaque area may be a calcified area.

Otherwise, the risk of plaque may be determined to be high when the brightness of the plaque area is less than a second critical value that is less than the first critical value. For example, if the brightness of the plaque area is less than the second critical value, the plaque area may include adipose tissue or necrotic tissue.

The risk of plaque may be determined to be low when the brightness of the plaque area is less than the first critical value and equal to or greater than the second critical value, and at the same time, when the brightness values in the plaque area are distributed evenly. For example, when the brightness of the plaque area is less than the first critical value and equal to or greater than the second critical value, and when the brightness values of the plaque area are distributed evenly, the plaque area may be a fibrosis area, but is not limited thereto.

A display 130 displays the generated ultrasound image. The display 130 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 130 according to exemplary embodiments.

The display 130 according to the present exemplary embodiment may display the risk of plaque, which is analyzed by the image processor 120. The display 130 may represent the risk of plaque by using at least one of color, a graph, and a numerical value.

For example, the display 130 may represent the risk of plaque as a color coordinate. A first axis of the color coordinate may denote a distribution state of the brightness values included in the plaque area, a second axis of the color coordinate may denote a brightness level of the plaque area, and a third axis of the color coordinate may denote a surface uniformity of the plaque area. Also, the display 130 may represent a first color corresponding to a first region on the first region included in the plaque area, and a second color corresponding to a second region on the second region included in the plaque area. In addition, the display 130 may mark an icon on a region having the highest risk from among a plurality of regions included in the plaque area. In addition, the display 130 may display a distribution state of the brightness values included in the plaque area as texture.

Figure 2:
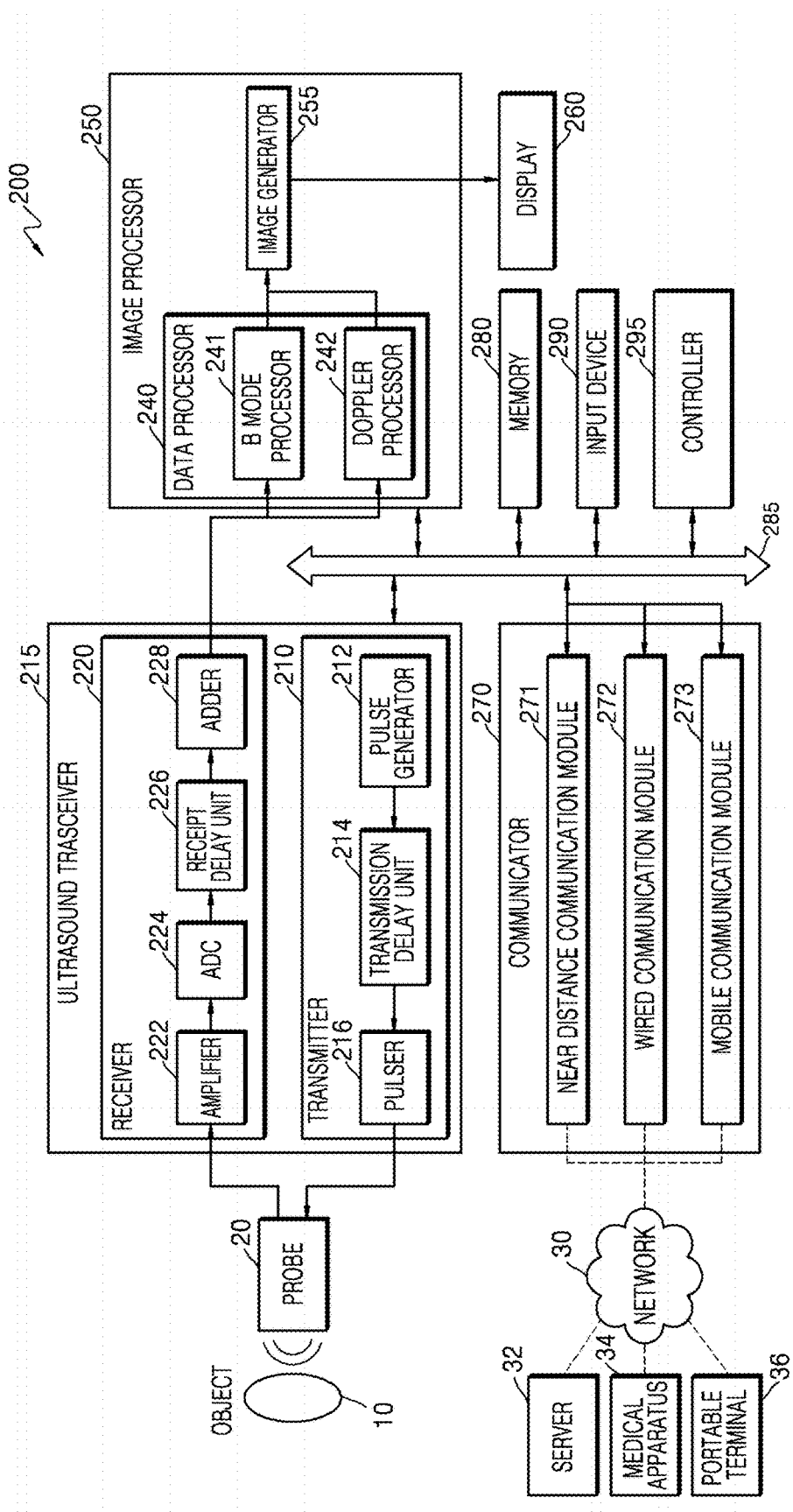
FIG. 2 is a block diagram of an ultrasound diagnosis apparatus according to an exemplary embodiment.

FIG. 2 is a block diagram of an ultrasound diagnosis apparatus 200 according to an exemplary embodiment.

Referring to FIG. 2, the ultrasound diagnosis apparatus 200 according to the present exemplary embodiment may include a probe 20, an ultrasound wave transceiver 215, an image processor 250, a communicator 270, a display 260, a memory 280, an input device 290, and a controller 295, and the above elements may be connected to each other via a bus 285.

The data acquirer 110 of FIG. 1 may correspond to the ultrasound wave transceiver 215 of FIG. 2, the image processor 120 of FIG. 1 may correspond to the image processor 250 of FIG. 2, and the display 130 of FIG. 1 may correspond to the display 260 of FIG. 2. Accordingly, descriptions of the elements 110, 120, and 130 of FIG. 1 may be also applied to the elements 215, 250, and 260 of FIG. 2, and thus, descriptions of the elements 215, 250, and 260 will be omitted.

In some exemplary embodiments, the ultrasound diagnosis apparatus 200 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 215 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 200 by wire or wirelessly, and according to exemplary embodiments, the ultrasound diagnosis apparatus 200 may include a plurality of probes 20.

A transmitter 210 supplies a driving signal to the probe 20. The transmitter 110 includes a pulse generator 212, a transmission delaying unit 214, and a pulser 216. The pulse generator 212 generates pulses for forming transmission ultrasound waves based on a predetermined pulse repetition frequency (PRF), and the transmission delaying unit 214 delays the pulses by delay times necessary for determining transmission directionality. The pulses which have been delayed respectively correspond to a plurality of piezoelectric vibrators included in the probe 20. The pulser 216 applies a driving signal (or a driving pulse) to the probe 20 based on timing corresponding to each of the pulses which have been delayed.

A receiver 220 generates ultrasound data by processing echo signals received from the probe 20. The receiver 120 may include an amplifier 222, an analog-to-digital converter (ADC) 224, a reception delaying unit 226, and a summing unit 228. The amplifier 222 amplifies echo signals in each channel, and the ADC 224 performs analog-to-digital conversion with respect to the amplified echo signals. The reception delaying unit 226 delays digital echo signals output by the ADC 124 by delay times necessary for determining reception directionality, and the summing unit 228 generates ultrasound data by summing the echo signals processed by the reception delaying unit 126. In some exemplary embodiments, the receiver 220 may not include the amplifier 222. In other words, if the sensitivity of the probe 20 or the capability of the ADC 224 to process bits is enhanced, the amplifier 222 may be omitted.

The image processor 250 generates an ultrasound image by scan-converting ultrasound data generated by the ultrasound transceiver 215 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing blood flow (also referred to as a color flow image), a tissue Doppler image showing a movement of tissue, or a spectral Doppler image showing a moving speed of an object as a waveform.

A B mode processor 241 extracts B mode components from ultrasound data and processes the B mode components. An image generator 255 may generate an ultrasound image indicating signal intensities as brightnesses based on the extracted B mode components 241.

Similarly, a Doppler processor 242 may extract Doppler components from ultrasound data, and the image generator 255 may generate a Doppler image indicating a movement of an object as colors or waveforms based on the extracted Doppler components.

According to an exemplary embodiment, the image generator 255 may generate a 3D ultrasound image via volume-rendering with respect to volume data and may also generate an elasticity image by imaging deformation of the object 10 due to pressure.

Furthermore, the image generator 255 may display various pieces of additional information in an ultrasound image by using text and graphics. In addition, the generated ultrasound image may be stored in the memory 280.

The display 260 may include at least one of a liquid crystal display (LCD), a thin film transistor-liquid crystal display (TFT-LCD), an organic light-emitting diode (OLED), a flexible display, a 3D display, and an electrophoretic display.

In addition, when the display 260 and a user input unit configure a layer structure to form a touch screen, the display 260 may be used as an input device through which information may be input by a touch of a user, in addition to an output device.

A touch screen may be configured to detect a touch pressure, as well as a touch input location and a touched area. Also, the touch screen may be configured to detect a proximity touch, as well as an actual touch.

The display 260 according to the present exemplary embodiment may display guide information related to a function corresponding to fingerprints recognized by the input device 290. In addition, if the display unit 260 includes the touch screen, guide information related to the function may be displayed on a point where the fingerprint is recognized.

The communication module 270 (communicator 270) is connected to a network 30 by wire or wirelessly to communicate with an external device or a server. The communication module 270 may exchange data with a hospital server or another medical apparatus in a hospital, which is connected thereto via a PACS. Furthermore, the communication module 270 may perform data communication according to the digital imaging and communications in medicine (DICOM) standard.

The communication module 270 may transmit or receive data related to diagnosis of an object, e.g., an ultrasound image, ultrasound data, and Doppler data of the object, via the network 30 and may also transmit or receive medical images captured by another medical apparatus, e.g., a CT apparatus, a MRI apparatus, or an X-ray apparatus. Furthermore, the communication module 270 may receive information about a diagnosis history or medical treatment schedule of a patient from a server and utilize the received information to diagnose the patient. Furthermore, the communication module 270 may perform data communication not only with a server or a medical apparatus in a hospital, but also with a portable terminal of a medical doctor or patient.

The communication module 270 is connected to the network 30 by wire or wirelessly to exchange data with a server 32, a medical apparatus 34, or a portable terminal 36. The communication module 270 may include one or more components for communication with external devices. For example, the communication module 1300 may include a local area communication module 271, a wired communication module 272, and a mobile communication module 273.

The local area communication module 271 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 272 refers to a module for communication using electric signals or optical signals. Examples of wired communication techniques according to an exemplary embodiment may include communication via a twisted pair cable, a coaxial cable, an optical fiber cable, and an Ethernet cable.

The mobile communication module 273 transmits or receives wireless signals to or from at least one selected from a base station, an external terminal, and a server on a mobile communication network. The wireless signals may be voice call signals, video call signals, or various types of data for transmission and reception of text/multimedia messages.

The memory 280 stores various data processed by the ultrasound diagnosis apparatus 200. For example, the memory 180 may store medical data related to diagnosis of an object, such as ultrasound data and an ultrasound image that are input or output, and may also store algorithms or programs which are to be executed in the ultrasound diagnosis apparatus 200.

The memory 280 may be any of various storage media, e.g., a flash memory, a hard disk drive, an electrically erasable programmable read-only memory (EEPROM), etc. Furthermore, the ultrasound diagnosis apparatus 100 may utilize web storage or a cloud server that performs the storage function of the memory 280 online.

The input device 290 refers to a unit via which a user inputs data for controlling the ultrasound diagnosis apparatus 50. The input device 290 may include hardware components, such as a keypad, a mouse, a touch pad, a touch screen, and a jog switch. In addition, the input device 290 may include a fingerprint sensor for recognizing fingerprints of the user. The input device 290 may further include any of various other input units including an electrocardiogram (ECG) measuring module, a respiration measuring module, a voice recognition sensor, a gesture recognition sensor, an iris recognition sensor, a depth sensor, a distance sensor, etc. In particular, the touch pad may include the touch screen configuring a layer structure with the display 260.

Here, the ultrasound diagnosis apparatus 200 according to the present exemplary embodiment may display an ultrasound image of a predetermined mode and a control panel for the ultrasound image on the touch screen. In addition, the ultrasound diagnosis apparatus 200 may sense a touch gesture of the user on the ultrasound image via the touch screen.

The ultrasound diagnosis apparatus 200 according to the present exemplary embodiment may include physical buttons that the user uses frequently from among buttons included in the control panel of a general ultrasound diagnosis apparatus, and may provide the other buttons as a GUI on the touch screen.

The controller 295 may control all operations of the ultrasound diagnosis apparatus 200. In other words, the controller 295 may control operations among the probe 20, the ultrasound transceiver 200, the image processor 250, the communication module 270, the memory 280, and the input device 290 shown in FIG. 1.

All or some of the probe 20, the ultrasound transceiver 215, the image processor 250, the display 240, the communication module 270, the memory 280, the input device 290, and the controller 295 may be implemented as software modules. However, exemplary embodiments of the present invention are not limited thereto, and some of the components stated above may be implemented as hardware modules. Also, at least one of the ultrasound transmission/reception unit 215, the image processor 250, and the communication module 270 may be included in the control unit 295; however, the inventive concept is not limited thereto.

Figure 3:
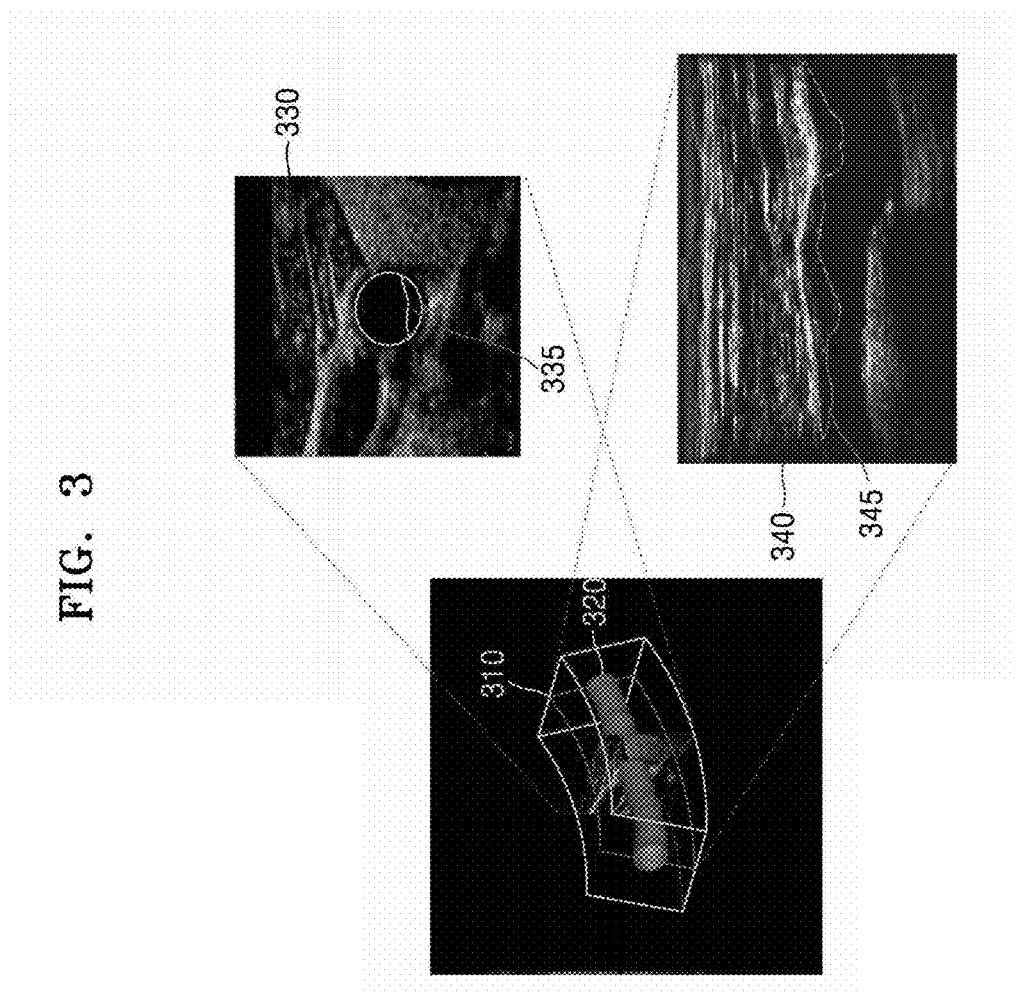
FIG. 3 is a diagram showing ultrasound data obtained according to an exemplary embodiment.

FIG. 3 is a diagram showing ultrasound data obtained according to an exemplary embodiment.

Referring to FIG. 3, the ultrasound diagnosis apparatus 100 according to the present exemplary embodiment may obtain 3D volume data 310 about an object, and the object may have blood vessels 320. The ultrasound diagnosis apparatus 100 transmits an ultrasound signal to the object and receives an echo signal reflected by the object, and processes the echo signal to generate ultrasound data. Here, the ultrasound diagnosis apparatus 100 may obtain the 3D volume data by using a phased probe, a linear probe, a convex probe, etc. The 3D volume data may denote data obtained by reconstructing 3D phase data from accumulated 2D data (data corresponding to cross-sectional ultrasound images) of the object.

The ultrasound diagnosis apparatus 100 according to the present exemplary embodiment may analyze a risk of plaque included in the blood vessel 320 by using cross-sectional images 330 and 340 corresponding to the 2D data included in the 3D volume data.

The ultrasound diagnosis apparatus 100 may extract a blood vessel area from the first ultrasound cross-sectional image 330 corresponding to a first cross-section included in the 3D volume data or the second ultrasound cross-sectional image 340 corresponding to a second cross-section. For example, the ultrasound diagnosis apparatus 100 may extract the blood vessel area by using an edge detection method as illustrated above with reference to FIG. 1, but is not limited thereto.

Also, the ultrasound diagnosis apparatus 100 may extract a plaque area included in the extracted blood vessel area. For example, the ultrasound diagnosis apparatus 100 may extract a first plaque area 335 from the first ultrasound cross-sectional image 330, and a second plaque area 345 from the second ultrasound cross-sectional image 340.

The ultrasound diagnosis apparatus 100 may analyze a risk of plaque corresponding to the first plaque area 335 and risk of a plaque corresponding to the second plaque area 345, based on surface shapes and brightness information of the first and second plaque areas 335 and 345, respectively. This will be described in more detail later.

FIGS. 4A to 5C are diagrams illustrating a method, performed by the ultrasound diagnosis apparatus 100, of determining a risk of plaque based on brightness information of the plaque area, according to an exemplary embodiment.

Figure 4A:
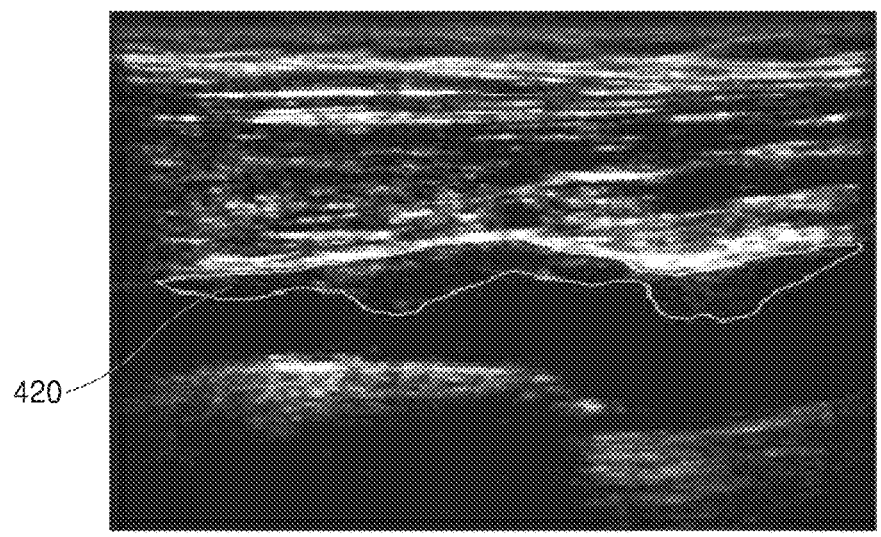
FIGS. 4A to 5C are diagrams illustrating a method, performed by the ultrasound diagnosis apparatus, of determining a risk of plaque based on brightness information of a plaque area, according to an exemplary embodiment.
Figure 4B:
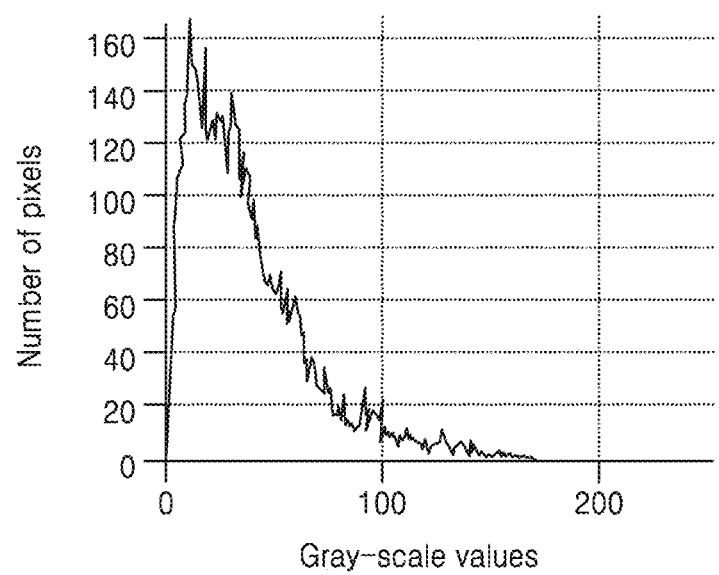

FIG. 4A shows a plaque area 420 extracted from an ultrasound image. Referring to FIG. 4B, the image processor 120 may represent brightness values of pixels included in the extracted plaque area 420 as a histogram. As shown in FIG. 4B, a histogram is a graph showing the number of pixels included in each of gray scale values. For example, a transverse axis denotes a brightness value of a pixel, and a longitudinal axis may denote the number of pixels.

The image processor 120 may calculate a median value, an average value, a minimum value, a maximum value, a distribution, and a standard deviation in the histogram. In addition, the image processor 120 may analyze a brightness level of the plaque area and a distribution state of the brightness values in the plaque area, by using the calculated values. For example, the brightness level of the plaque area may be determined as the median value or the average value calculated from the histogram. In addition, the distribution state of the brightness values in the plaque area may be determined by the distribution or the standard deviation calculated from the histogram. However, one or more exemplary embodiments are not limited to the above examples.

The image processor 120 may determine the risk of plaque according to the brightness level of the plaque area and the distribution state of the brightness values in the plaque area.

Figure 5C:
Figure 5B:
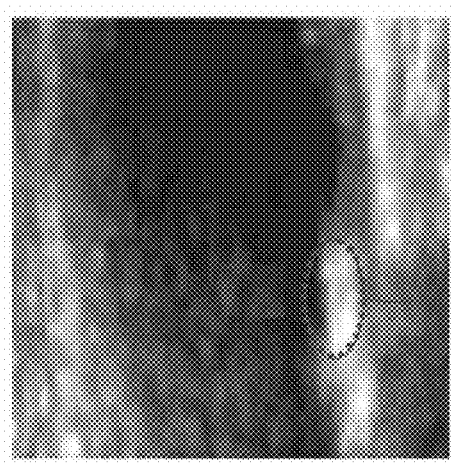
Figure 5A:
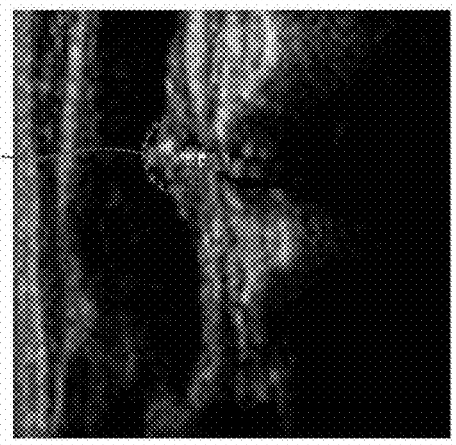

For example, as shown in FIG. 5A, when the brightness level of a first plaque area 510 is less than a first critical value and equal to or less than a second critical value that is less than the first critical value, and when the brightness values in the first plaque area 510 is distributed evenly, the image processor 120 may determine the risk of plaque corresponding to the first plaque area 510 to be low. Here, the first plaque area 510 may be a fibrosis area.

As shown in FIG. 5B, when the brightness level of a second plaque area 520 is equal to or greater than the first critical value, the image processor 120 may determine the risk of plaque corresponding to the second plaque area 520 to be high. Here, the second plaque area 520 may be a calcified area.

As shown in FIG. 5C, when the brightness level of a third plaque area 530 is less than the second critical value, the image processor 120 may determine the risk of plaque corresponding to the third plaque area 530 to be hight. Here, the third plaque area 530 may be an area having an adipose tissue or a necrosis.

Figure 6A:
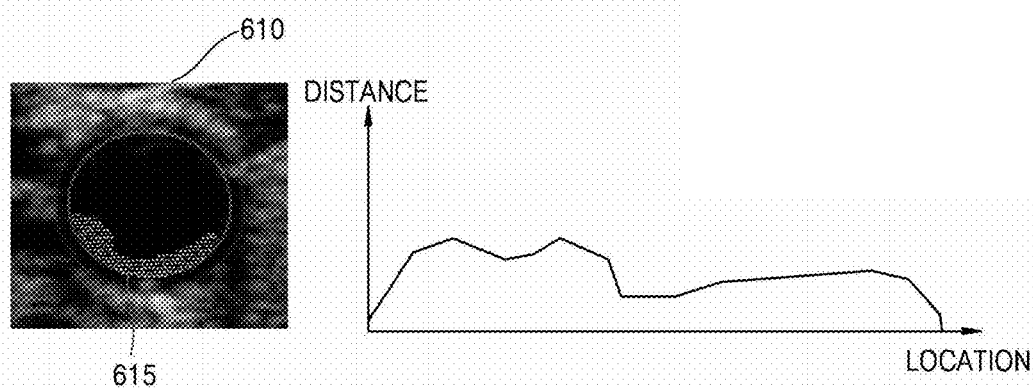
FIGS. 6A and 6B are diagrams illustrating a method, performed by the ultrasound diagnosis apparatus, of determining a risk of plaque based on a surface shape of a plaque area, according to an exemplary embodiment.
Figure 6B:
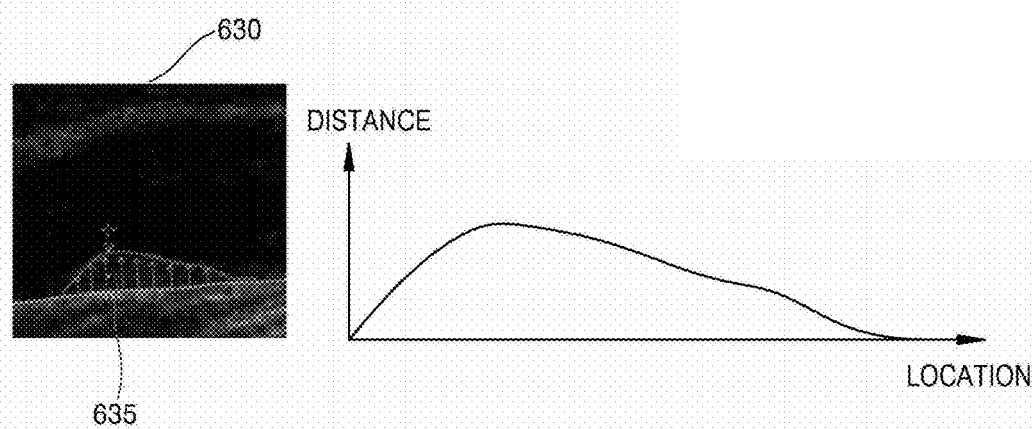

FIGS. 6A and 6B are diagrams illustrating a method, performed by the ultrasound diagnosis apparatus 100, of determining a risk of plaque according to a surface shape of a plaque area, according to an exemplary embodiment.

Referring to FIG. 6A, a first ultrasound image 610 shows a cross-section of a blood vessel perpendicular to a lengthwise direction of the blood vessel. The image processor 120 may measure minimum distances from a surface of a blood vessel intima to a surface of a plaque area 615 in a circumferential direction of the blood vessel, by using the first ultrasound image 610. In addition, a first graph of FIG. 6A shows measured distance values according to locations of measuring the distance in the first ultrasound image 610.

Accordingly, the image processor 120 may analyze the surface uniformity of the plaque area in the circumferential direction of the blood vessel, by using the first graph. For example, the image processor 120 may calculate an SI by using an average of the distance values and the standard deviation in the first graph. Here, the SI may be represented as a ratio of the average with respect to the standard deviation. The image processor 120 may determine from analysis that the surface of the plaque area is uniform when the SI is equal to or greater than 1, and accordingly, the image processor 120 may determine the risk of plaque to be low. On the contrary, when the SI is less than 1, the image processor 120 may determine from analysis that the surface of the plaque area is not uniform and determine the risk of plaque to be high. However, one or more exemplary embodiments are not limited to the above examples.

In addition, referring to FIG. 6B, a second ultrasound image 630 shows a cross-section of the blood vessel in the lengthwise direction of the blood vessel.

The image processor 120 may measure distances from a surface of the blood vessel intima to a surface of the plaque area in the second ultrasound image 630, by using the method illustrated with reference to FIG. 6A. In addition, a second graph of FIG. 6B shows measured distance values according to locations from where the distances in the second ultrasound image 630 were measured.

Accordingly, the image processor 120 may calculate an SI of the blood vessel in the lengthwise direction of the blood vessel by using the second graph, and may analyze the surface uniformity of the plaque area by using the SI. In addition, the image processor 120 may determine the risk of plaque according to the surface uniformity of the plaque area.

Figure 7:
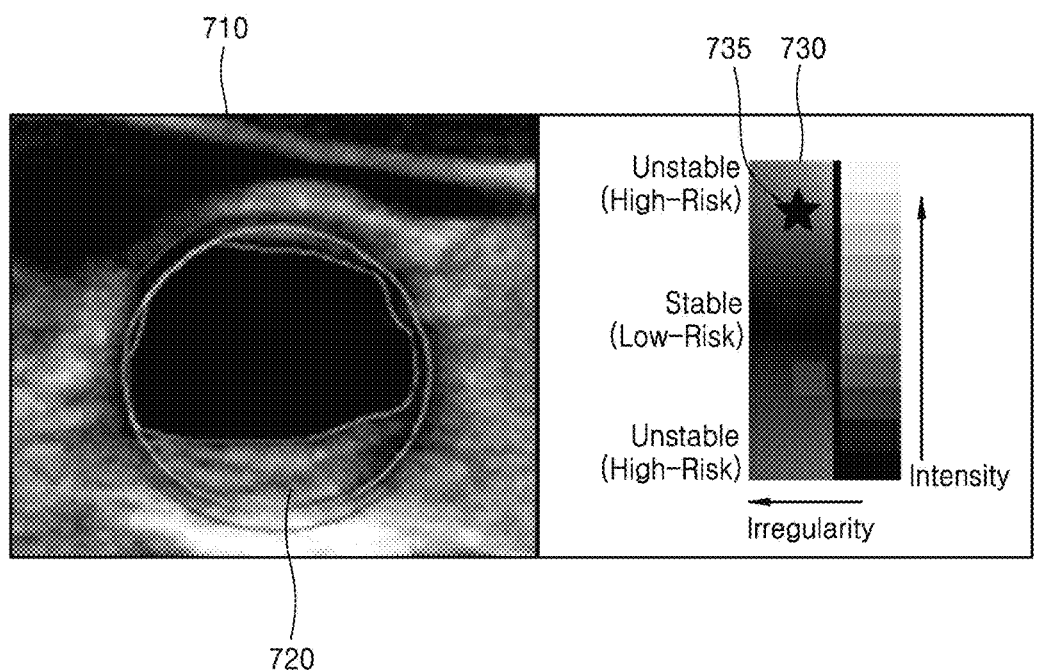
FIG. 7 is a diagram showing an example of displaying a risk of plaque analyzed according to an exemplary embodiment on a display.

FIG. 7 is a diagram showing an example, in which the risk of plaque analyzed according to an exemplary embodiment is displayed on the display 130.

Referring to FIG. 7, the display 130 may display an ultrasound image 710 on a first region. Here, the ultrasound image 710 is an ultrasound cross-sectional image showing a blood vessel, and the ultrasound image 710 may include a plaque area 720 extracted from the blood vessel area.

In addition, the display 130 may represent the risk of plaque as a color coordinate 730 on a second region. For example, a transverse axis of the color coordinate 730 represents a distribution state (irregularity) of brightness values in the plaque area 720, and a longitudinal axis represents a brightness level of the plaque area 720. Here, the color coordinate 730 may represent a transverse coordinate or longitudinal coordinate in different colors.

For example, when the brightness level of the plaque area has a y1 value and the SI has a x1 value, color at a (x1, y1) coordinate in the color coordinate 730 may be determined as the color representing the risk of plaque corresponding to the plaque area. In addition, an icon 735 may be marked on the (x1, y1) coordinate. Also, the plaque area 720 may be displayed in the determined color.

In addition, although FIG. 7 shows the color coordinate 730, in which the distribution state of the brightness values in the plaque area is represented in the transverse axis and the brightness level of the plaque area is represented in the longitudinal axis, one or more exemplary embodiments are not limited thereto. The transverse axis of the color coordinate may represent one of the distribution state of the brightness values in the plaque area, the brightness level of the plaque area, and the surface uniformity of the plaque area, and the longitudinal axis may represent one of the other, except for the parameter represented by the transverse axis.

Accordingly, the user may recognize the location of the color representing the risk of plaque corresponding to the plaque area in the color coordinate so as to identify the risk of plaque corresponding to the plaque area.

In addition, FIG. 7 shows an example, in which the risk of plaque is represented as a 2D color coordinate, but the risk of plaque may be represented as a 3D color coordinate. For example, in the 3D color coordinate, a first axis may denote a distribution state of the brightness values in the plaque area, a second axis may denote a brightness level of the plaque area, and a third axis may denote a surface uniformity of the plaque area.

Here, the 3D color coordinate may be represented by the color varying according to the coordinate on the first axis, the coordinate on the second axis, or the coordinate on the third axis. For example, when the distribution state (non-uniformity) of the brightness values in the plaque area has an x1 value, the brightness level of the plaque area has a y1 value, and a surface uniformity of the plaque area has a z1 value, a color represented at a (x1, y1, z1) coordinate in the 3D color coordinate may be determined as the color representing the risk of plaque corresponding to the plaque area. In addition, an icon may be marked on the (x1, y1, z1) coordinate, and the plaque area may be represented in the determined color.

Figure 8:
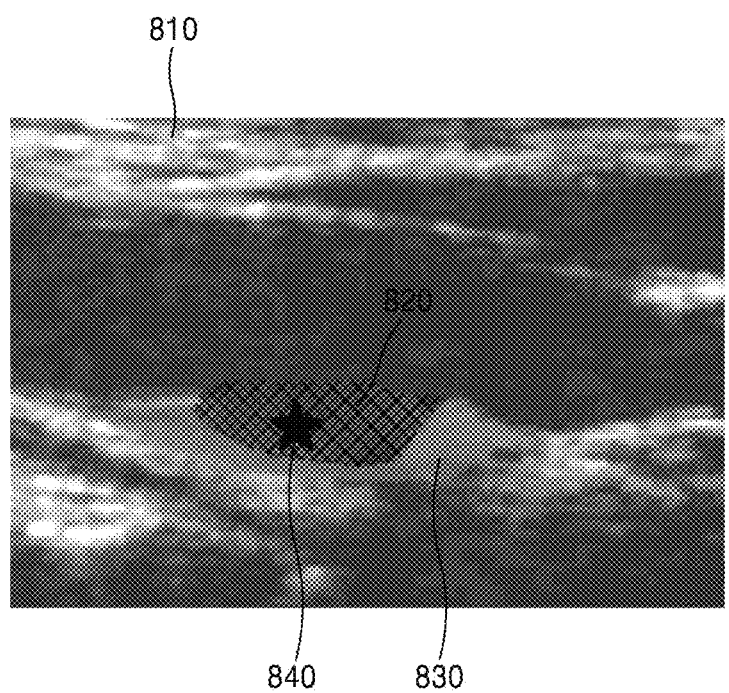
FIG. 8 is a diagram showing an example of displaying a risk of plaque analyzed according to an exemplary embodiment on a display.

FIG. 8 is a diagram showing an example of displaying risk of plaque analyzed according to an exemplary embodiment, on the display 120.

Referring to FIG. 8, the display 120 may display an ultrasound image 810. Here, the ultrasound image 810 may be an ultrasound cross-sectional image showing a blood vessel, and may include a plaque area extracted from the blood vessel.

The plaque area may be represented by a color. As illustrated above with reference to FIG. 7, a color represents the risk of plaque that is analyzed based on at least one of the distribution state of the brightness values in the plaque area, the brightness level of the plaque area, and the surface uniformity of the plaque area.

The image processor 120 may divide the plaque area into a plurality of regions according to features of the plaque area to analyze the risk of plaque corresponding to each of the plurality of regions.

For example, as shown in FIG. 8, the image processor 120 may divide the plaque area into a first region 820 and a second region 830, and may analyze the risk of plaque corresponding to the first region 820 and the risk of plaque corresponding to the second region 830. Accordingly, the first region 820 is represented by a first color (e.g., red color) corresponding to the risk of plaque corresponding to the first region 820, and the second region 830 may be represented by a second color (e.g., green color) corresponding to the risk of plaque corresponding to the second region 830.

In addition, the display 130 may mark an icon on a region having the highest risk from among the plurality of regions. For example, an icon 840 may be marked on the first region 820 having a higher risk between the first and second regions 820 and 830.

Figure 9:
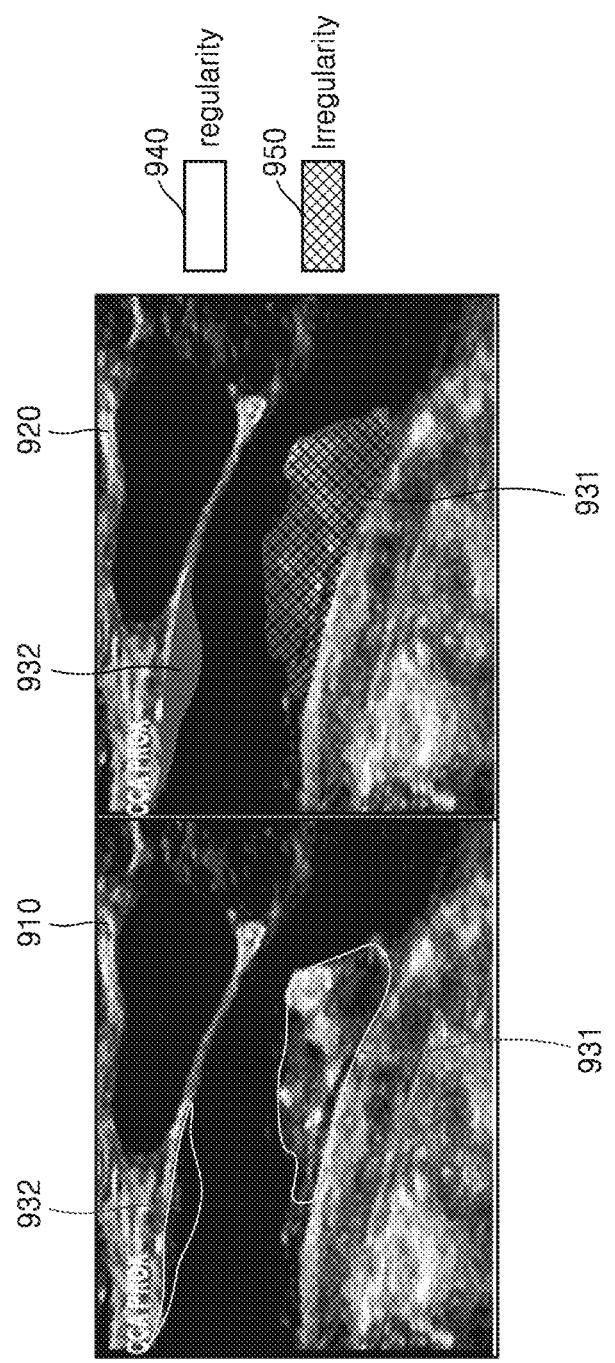
FIG. 9 is a diagram showing an example of displaying a risk of plaque analyzed according to an exemplary embodiment on a display.

FIG. 9 is a diagram showing an example of displaying a risk of plaque on the display 130, according to an exemplary embodiment.

Referring to FIG. 9, the display 130 may display a first ultrasound image 910 on a first region. Here, the first ultrasound image 910 may be an ultrasound cross-sectional image of a blood vessel, and the first ultrasound image 910 may include a first plaque area 931 and a second plaque area 932 extracted from the blood vessel.

In addition, the display 130 may display a second ultrasound image 920 representing risks of the plaque areas on a second region. The risks of the plaque areas may be represented in colors.

For example, as illustrated above with reference to FIG. 7, colors representing the risks of plaque, which are analyzed based on at least one of the distribution state of the brightness values in the plaque area, the brightness level of the plaque area, and the surface uniformity of the plaque area, may be represented on the first and second plaque areas 931 and 932.

In addition, the display 130 may represent the distribution state of the brightness values in the plaque area by using textures. For example, if the brightness of the first plaque area 931 is not evenly distributed, the first plaque area 931 may be represented by a first texture 950. If the brightness of the second plaque area 932 is evenly distributed, the second plaque area 932 may be represented by a second texture 940.

Figure 10:
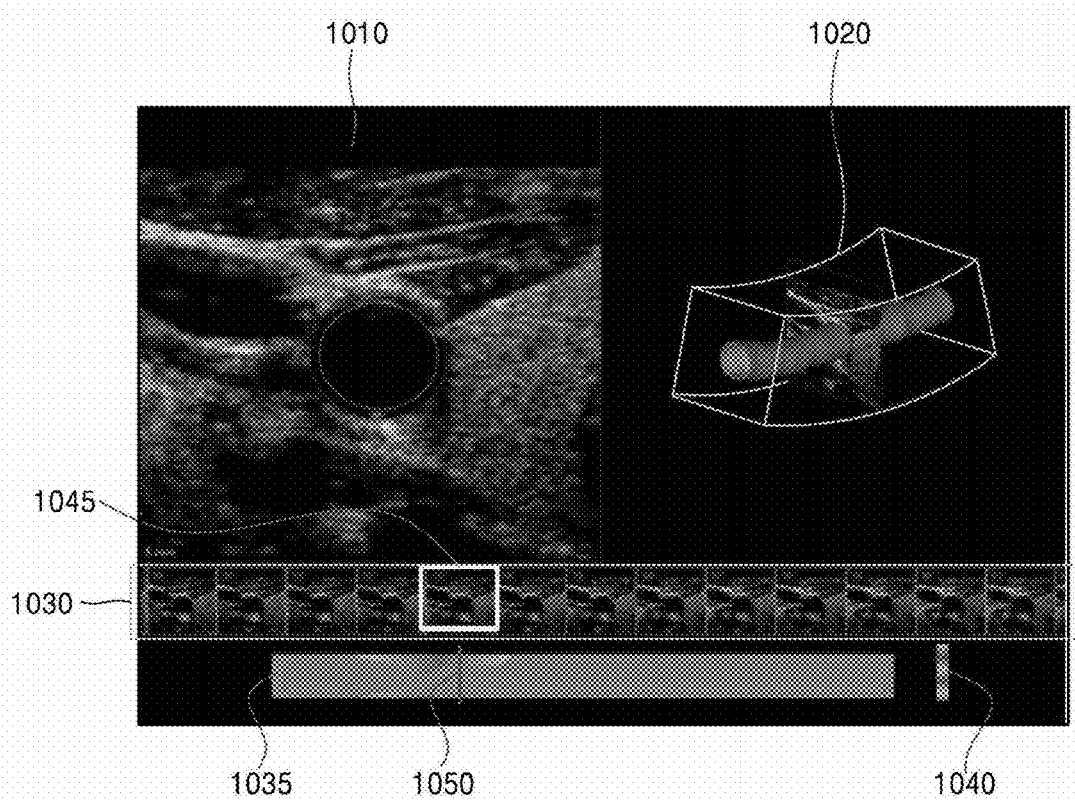
FIG. 10 is a diagram showing an example of displaying a risk of plaque analyzed according to an exemplary embodiment.

FIG. 10 is a diagram showing an example of displaying a risk of plaque on the display 130, according to an exemplary embodiment.

Referring to FIG. 10, the display 130 may display 3D volume data 1020 of an object on a first region. Here, the 3D volume data 1020 may be ultrasound volume data showing a blood vessel, and may include a plurality of cross-sections.

The display 130 may display on a second region, an ultrasound cross-sectional image 1010 corresponding to one of the plurality of cross-sections included in the 3D volume data 1020. Here, the ultrasound cross-sectional image 1010 displayed on the second region may be an ultrasound cross-sectional image corresponding to a cross-section selected based on a user input.

The display 130 may display ultrasound cross-sectional images 1030 respectively corresponding to the cross-sections included in the 3D volume data, on a third region. From among the ultrasound cross-sectional images 1030 displayed on the third region, an ultrasound cross-sectional image 1045 that corresponds to the ultrasound cross-sectional image 1020 displayed on the second region may be highlighted. For example, a square box may be marked on boundaries of the ultrasound cross-sectional image 1045 corresponding to the ultrasound cross-sectional image displayed on the second region.

The display 130 may display a color bar 1035 representing a shape of the plaque and the risk of plaque on a fourth region.

The color bar 1035 represents a thickness of the plaque area corresponding to a distance from a surface of the blood vessel intima to a surface of the plaque area, and represents a color corresponding to the risk of plaque corresponding to the plaque area. Here, the color corresponding to the risk of plaque corresponding to the plaque area may be determined based on a one-dimensional (1D) color coordinate 1040. Here, as a color is located at a lower part of the first color coordinate 140, the color represents a higher risk, and as a color is located at an upper part of the first color coordinate 140, the color represents a lower risk, but is not limited thereto.

Due to the use of the color bar 1035 representing the thickness of the plaque area and the risk of plaque corresponding to the plaque area, the user may easily identify the thickness of the plaque area and a degree of angiostenosis.

Also, when a line 1050 on the color bar 1035 is moved to left and right sides to be located at an aribitrary position, a cross-sectional image at the corresponding position is selected from among the plurality of ultrasound cross-sectional images 1030 displayed on the third region, and the selected cross-sectional image may be displayed on the second region.

Figure 11A:
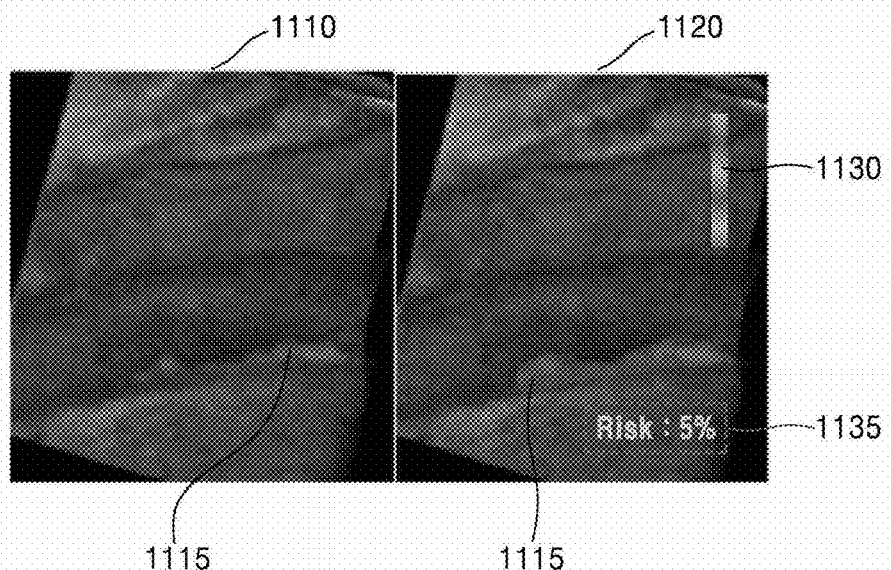
FIGS. 11A and 11B are diagrams showing an example of displaying a risk of plaque analyzed according to an exemplary embodiment.
Figure 11B:
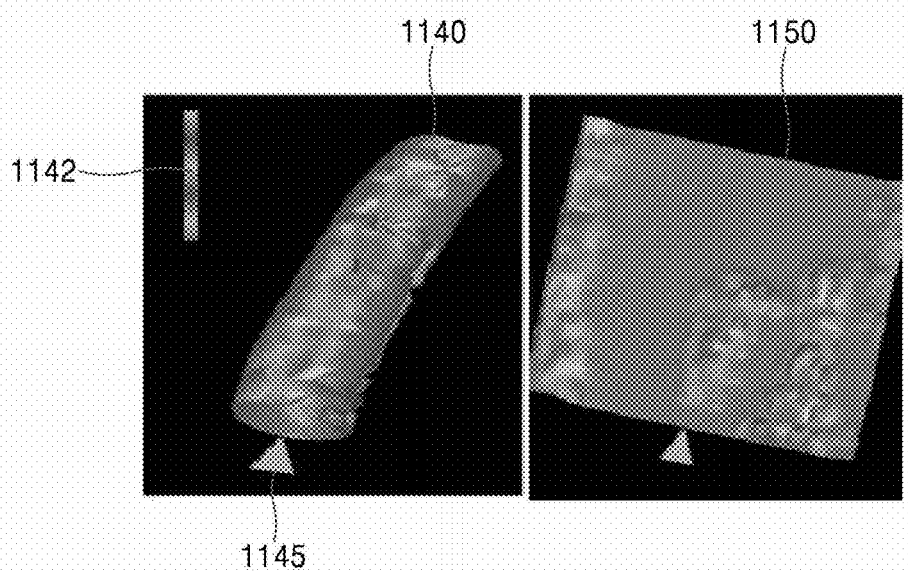

FIGS. 11A and 11B are diagrams showing an example of displaying a risk of plaque on the display 130, according to an exemplary embodiment.

Referring to FIG. 11A, the display 130 may display a first ultrasound image 1110 on a first region. Here, the first ultrasound image 1110 is a 3D ultrasound image showing a blood vessel, and may include a plaque area 1115 extracted from the blood vessel.

In addition, the display 130 may display a second ultrasound image 1120 in which a risk of plaque corresponding to the plaque area 1115 is represented on a second region. The second ultrasound image 1120 may include the color representing the risk of plaque corresponding to the plaque area expressed on the plaque area of the first ultrasound image 1110. In addition, the display 130 may represent the risk of plaque corresponding to the plaque area 1115 as a numerical value 1135.

Referring to FIG. 11B, the display 130 may display a 3D model 1140 of a blood vessel on a first region. Here, the 3D model 1140 includes the plaque area represented by a color, and the color of the plaque denotes the risk of plaque corresponding to the plaque area.

In addition, the display 130 may display a plane color image 1150 that is obtained by spreading the 3D model of a cylindrical shape in the first region about a reference point 1145.

Figure 12:
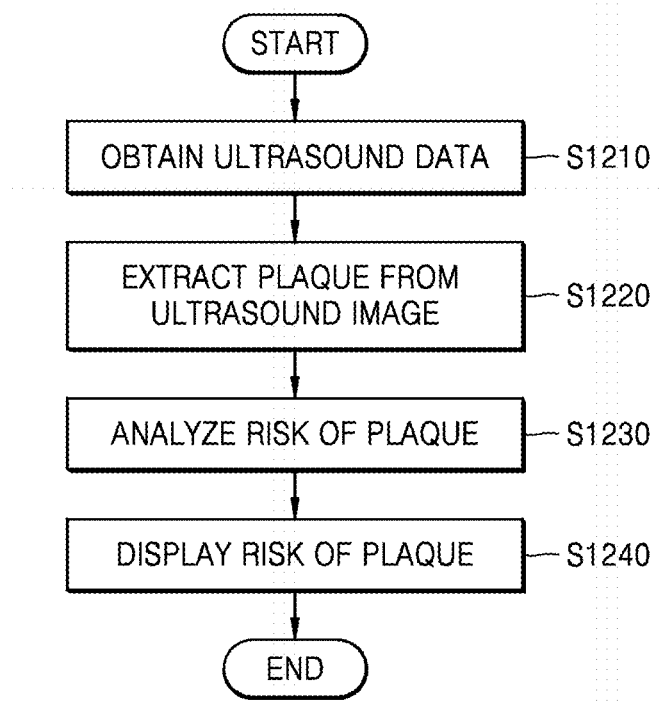
FIG. 12 is a flowchart illustrating a method of operating an ultrasound diagnosis apparatus, according to an exemplary embodiment.

FIG. 12 is a flowchart illustrating a method of operating an ultrasound diagnosis apparatus 100, according to an exemplary embodiment.

Referring to FIG. 12, the ultrasound diagnosis apparatus 100 may obtain ultrasound data (S1210).

For example, the ultrasound diagnosis apparatus 100 transmits an ultrasound signal to an object having blood vessels, and receives an echo signal reflected by the object. The ultrasound diagnosis apparatus 100 processes the echo signal to generate ultrasound data about the object having the blood vessels.

The ultrasound diagnosis apparatus 100 extracts a blood vessel from the ultrasound image, and extracts a plaque area included in the blood vessel (S1220).

For example, the ultrasound diagnosis apparatus 100 may generate an ultrasound image through a scan conversion process performed on the ultrasound data. The ultrasound diagnosis apparatus 100 may extract a B mode component from the ultrasound data, and may generate the ultrasound image in which an intensity of the signal is expressed as a brightness based on the extracted B mode component.

In addition, the ultrasound diagnosis apparatus 100 may extract a blood vessel area from the generated ultrasound image. For example, the ultrasound diagnosis apparatus 100 may extract the blood vessel area by using an edge detection method, as illustrated above with reference to FIG. 1. However, one or more exemplary embodiments are not limited thereto, and various blood vessel extraction methods that are well known in the art may be used to extract the blood vessel area from the ultrasound image.

In addition, the ultrasound diagnosis apparatus 100 may extract the plaque area included in the blood vessel area. For example, the ultrasound diagnosis apparatus 100 may extract the plaque area by using the methods described above with reference to FIG. 1. However, one or more exemplary embodiments are not limited thereto, and the plaque area may be extracted from the ultrasound image by using various plaque extraction methods that are well known in the art.

The ultrasound diagnosis apparatus 100 may analyze the risk of plaque corresponding to the extracted plaque area (S1230).

The ultrasound diagnosis apparatus 100 may analyze the risk of plaque based on the surface shape of the extracted plaque area and brightness information of the plaque area.

For example, the ultrasound diagnosis apparatus 100 may calculate an SI representing whether the surface of the plaque area is uniform, and may determine the risk of plaque according to the SI. Alternatively, the ultrasound diagnosis apparatus 100 may determine the risk of plaque corresponding to the plaque area according to the brightness level of the plaque area and a distribution state of the brightness values in the plaque area.

The ultrasound diagnosis apparatus 100 may display the risk of plaque corresponding to the plaque area (S1240).

The ultrasound diagnosis apparatus 100 may represent the risk of plaque by using at least one of the color, a graph, and a numerical value.

For example, the ultrasound diagnosis apparatus 100 may display the risk of plaque as a color coordinate. A first axis of the color coordinate may represent the distribution state of the brightness values in the plaque area, a second axis may represent a brightness level of the plaque area, and a third axis may represent a surface uniformity of the plaque area. In addition, the ultrasound diagnosis apparatus 100 may represent a first region included in the plaque area in a first color corresponding to a risk of plaque corresponding to the first region, and may represent a second region included in the plaque area in a second color corresponding to a risk of plaque corresponding to the second region. In addition, the ultrasound diagnosis apparatus 100 may mark an icon on a region having the highest risk from among a plurality of regions included in the plaque area. In addition, the ultrasound diagnosis apparatus 100 may represent the distribution state of the brightness values in the plaque area by using a texture.

One or more exemplary embodiments may also be embodied as computer readable codes on a non-transitory computer readable recording medium. The non-transitory computer readable recording medium is any data storage device that can store data which can thereafter be read by a computer system. Examples of the non-transitory computer readable recording medium include read-only memory (ROM), random-access memory (RAM), CD-ROMs, magnetic tapes, floppy disks, optical data storage devices, etc. The non-transitory computer readable recording medium can also be distributed over network coupled computer systems so that the computer readable code is stored and executed in a distributive manner.

According to one or more exemplary embodiments, risk of plaque is analyzed according to a surface shape of a plaque area and brightness information of the plaque area in a blood vessel ultrasound image, and accordingly, the risk of plaque may be accurately determined.

In addition, the risk of plaque may be expressed in various ways so that the user may easily recognize the risk of plaque and may obtain various information about the plaque.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. An ultrasound diagnosis apparatus comprising:
an ultrasound probe configured to obtain ultrasound data of an object having blood vessels;
an image processor configured to:
extract a blood vessel area from an ultrasound image generated based on the ultrasound data,
extract a plaque area included in the blood vessel area,
determine a risk of plaque based on at least one of brightness information of the plaque area or a distribution state of brightness values of the plaque area, wherein the risk of plaque is determined to be high when a brightness level of the plaque area is equal to or greater than a first critical value or less than a second critical value that is less than the first critical value, and the risk of plaque is determined to be low when the brightness level of the plaque area is less than the first critical value and equal to or greater than the second critical value and the distribution state of the brightness values of the plaque area satisfies a predetermined criteria, and
determine a color representing the risk of plaque, based on the brightness level of the plaque area and the distribution state of the brightness values of the plaque area, by referencing a color map that correlates brightness levels and the distribution states of brightness values to colors representing the risk of plaque; and
a display configured to display the risk of plaque as the determined color.

2. The ultrasound diagnosis apparatus of claim 1, wherein the image processor is configured to determine a surface shape of the plaque area, calculate a smoothness index (SI) representing a surface uniformity of the plaque area, based on the determined surface shape, and determine the risk of plaque based on the surface uniformity of the plaque area, and the risk of plaque is determined to be low when a surface of the plaque area is uniform and is determined to be high when the surface of the plaque area is not uniform.

3. The ultrasound diagnosis apparatus of claim 2, wherein the image processor is configured to measure distances from a surface of a blood vessel to a surface of the plaque area in at least one of a circumferential direction or a lengthwise direction of the blood vessel, and calculate the SI of the plaque area based on a distribution of the measured distances.

4. The ultrasound diagnosis apparatus of claim 1, wherein the image processor is configured to calculate the brightness level of the plaque area and the distribution state of the brightness values, based on a histogram of the brightness values of the plaque area.

5. The ultrasound diagnosis apparatus of claim 4, wherein a value representing the distribution state of the brightness values is calculated based on at least one of a median value, an average value, a minimum value, a maximum value, a distribution value, or a standard deviation calculated from the histogram.

6. The ultrasound diagnosis apparatus of claim 1, wherein the display is configured to display the risk of plaque by using at least one of a graph or a numerical value.

7. The ultrasound diagnosis apparatus of claim 1, wherein the display is configured to indicate on a first region included in the plaque area a first color corresponding to a risk of plaque in the first region, and indicate a second color on a second region included in the plaque area corresponding to a risk of plaque in the second region.

8. The ultrasound diagnosis apparatus of claim 7, wherein the display is configured to mark an icon on a region having a higher risk between the first region and the second region.

9. The ultrasound diagnosis apparatus of claim 1, wherein the display is configured to indicate the distribution state of the brightness values of the plaque area as a texture.

10. A method of operating an ultrasound diagnosis apparatus, the method comprising:
obtaining ultrasound data of an object having blood vessels;
extracting a blood vessel area from an ultrasound image generated based on the ultrasound data, and extracting a plaque area included in the blood vessel area;
determining a risk of plaque based on at least one of brightness information of the plaque area or a distribution state of brightness values of the plaque area, wherein the risk of plaque is determined to be high when a brightness level of the plaque area is equal to or greater than a first critical value or less than a second critical value that is less than the first critical value, and the risk of plaque is determined to be low when the brightness level of the plaque area is less than the first critical value and equal to or greater than the second critical value and the distribution state of brightness values of the plaque area satisfies a predetermined criteria;
determining a color representing the risk of plaque, based on the brightness level of the plaque area and the distribution state of the brightness values of the plaque area by referencing a color map that correlates brightness levels and distribution states of brightness values to colors representing the risk of plaque; and
displaying the risk of plaque as the determined color.

11. The method of claim 10, wherein the determining of the risk of plaque comprises:
determining a surface shape of the plague area;
calculating a smoothness index (SI) representing a surface uniformity of the plaque area, based on the determined surface shape; and
determining the risk of plaque based on the surface uniformity of the plaque area,
wherein the risk of plaque is determined to be low when the surface of the plaque area is uniform, and is determined to be high when the surface of the plaque area is not uniform.

12. The method of claim 11, wherein the calculating of the SI comprises:
measuring distances from a surface of the blood vessel to the surface of the plaque area in at least one of a circumferential direction or a lengthwise direction of the blood vessel; and
calculating the SI of the plaque area based on a distribution of the measured distances.

13. The method of claim 10, wherein the determining of the risk of plaque comprises calculating the brightness level of the plaque area and the distribution state of the brightness values based on a histogram of the brightness values of the plaque area.

14. The method of claim 13, wherein a value representing the distribution state of the brightness values is calculated based on at least one of a median value, an average value, a minimum value, a maximum value, a distribution value, or a standard deviation calculated from the histogram.

15. The method of claim 10, wherein the displaying of the risk of plaque comprises indicating the risk by using at least one of a graph or a numerical value.

16. The method of claim 10, wherein the displaying of the risk of plaque comprises indicating on a first region included in the plaque area a first color corresponding to a risk of plaque in the first region, and indicating on a second region included in the plaque area a second color corresponding to a risk of plaque in the second region.

17. The method of claim 16, wherein the displaying of the risk of plaque comprises marking an icon on a region having a higher risk between the first region and the second region.

18. The method of claim 10, wherein the displaying of the risk of plaque comprises indicating the distribution state of the brightness values of the plaque area as a texture.

* * * * *